United States Patent [19]

Thistlethwaite et al.

[11] Patent Number: 5,402,240
[45] Date of Patent: Mar. 28, 1995

[54] SPERM DENSIMETER

[75] Inventors: Douglas W. Thistlethwaite, Mira Loma; Jack E. Peterson, West Covina; James N. Dupree, Chino Hills, all of Calif.

[73] Assignee: Dupree, Inc., Chino, Calif.

[21] Appl. No.: 197,742

[22] Filed: Feb. 17, 1994

[51] Int. Cl.$^6$ .......................................... G01N 21/00
[52] U.S. Cl. .................................................... 356/433
[58] Field of Search ............... 356/433, 434, 436, 307, 356/435

[56] References Cited

U.S. PATENT DOCUMENTS

| | | | |
|---|---|---|---|
| 3,684,378 | 8/1972 | Lord | 356/434 |
| 4,050,821 | 9/1977 | Cuthbert et al. | 356/433 |
| 4,566,798 | 1/1986 | Haas | 356/243 |
| 4,589,774 | 5/1986 | Dupree et al. | 356/436 |
| 4,632,562 | 12/1986 | Dupree et al. | 356/436 |
| 4,878,755 | 11/1989 | Siegmund et al. | 356/382 |

Primary Examiner—Richard A. Rosenberger
Attorney, Agent, or Firm—Harris, Wallen MacDermott & Tinsley

[57] ABSTRACT

An instrument for measuring sperm concentration and calculating dose value and having an optical assembly with a light source, a specimen holder and a photodetector, a computation unit, a display, and a storage unit for storing a concentration calculation equation. The computation unit provides for calculating sperm concentration using the stored concentration calibration equation and a sample transmittance value, the optical assembly provides for measuring transmission of the specimen holder while empty with the light source energized, sample transmission of the specimen holder with a semen specimen with the light source energized, and dark cell output of said photodetector with said light source unenergized, and dark cell output of said photodetector with said light source unenergized, and said computation unit further provides for calculating actual sample percent transmission.

8 Claims, 12 Drawing Sheets

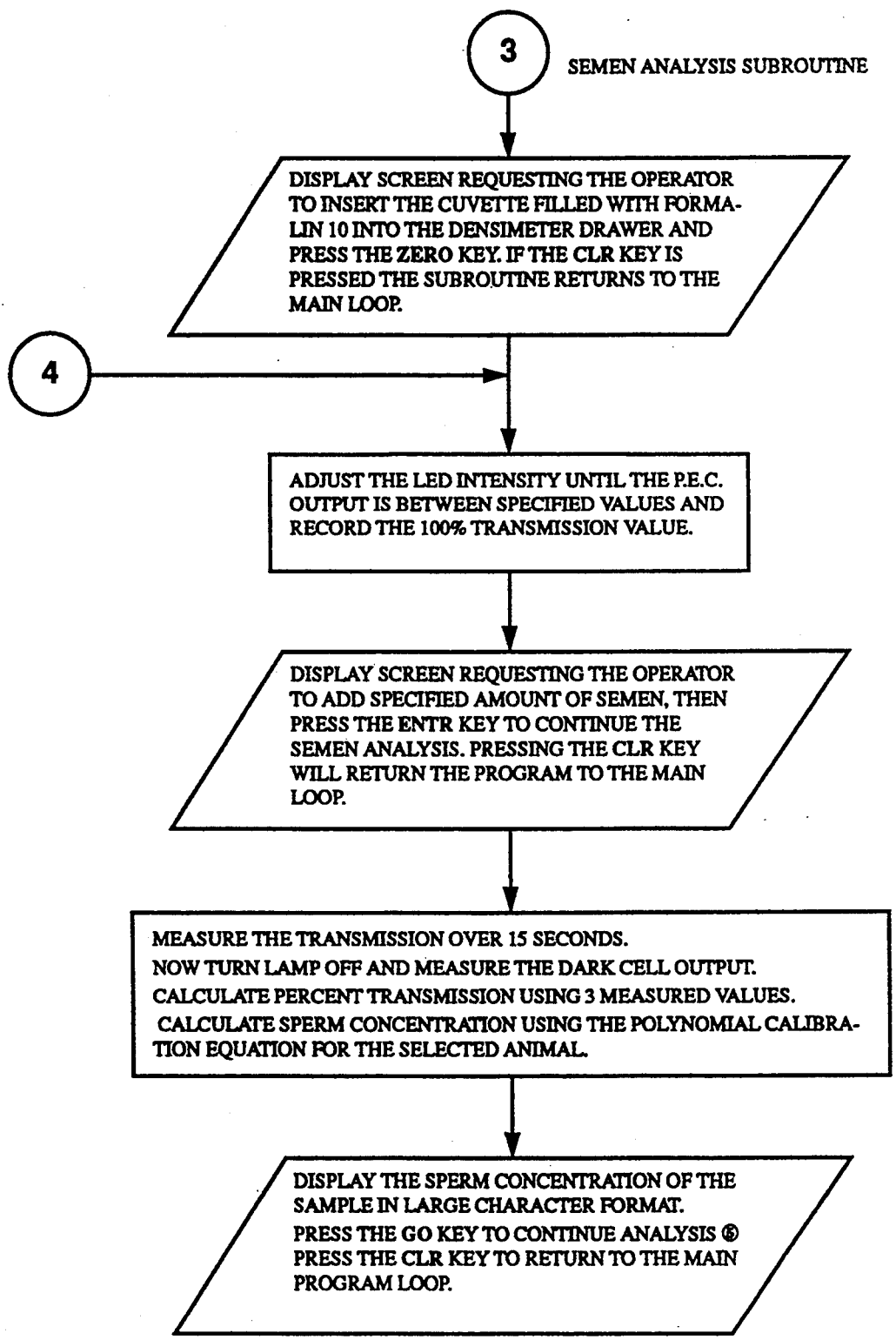

PROGRAM FLOW CHART

SPERM DENSIMETER

CROSS-REFERENCE TO RELATED PATENTS

This application is related to U.S. Pat. Nos. 4,589,774 and 4,632,562 which have the same assignee as the present application.

BACKGROUND OF THE INVENTION

This invention relates to new and improved apparatus and method for the measurement of the sperm density in a semen specimen and the determination of dosages for artificial insemination.

When properly practiced, artificial insemination (AI) can be a highly successful management technique for improving the reproductive efficiency of various domestic animals.

AI is widely practiced in the cattle breeding industry and is finding increasing use in equine (all breeds except thoroughbred) reproduction; and is being used, at least experimentally in the breeding of canines and other animals.

There are many specific reasons for the practice of AI, most of which ultimately reduce to a matter of economics. For example, an AI program conducted by competent practitioners using proven techniques and equipment can reduce the occurrence of injury to valuable animals and diminish the transmission of certain reproductive system diseases. Additionally, and of major importance, a maximum number of females can be brought into pregnancy in minimum time and the number of progeny from males of recognized genetic superiority can be greatly increased.

Although the detailed procedures and the apparatus used in an AI program vary with the characteristics and anatomy of the various species, the handling, processing and evaluation of semen in the field laboratory is nearly the same for all animals.

In some species, such as the equine, the ejaculate contains a gel-like substance which has no bearing on fertilization but does interfere with laboratory evaluation and insemination procedures. The gel is removed at the time of collection by passing the ejaculate through an appropriate filter prior to its entry into the holding container.

It is important that the semen be protected from sunlight and that it be held at nearly constant animal body temperature from the time that it is collected until laboratory analysis is completed. All apparatus and containers that will come into contact with semen that is to remain viable must be clean and warmed to body temperature before use. A sample of a uniform mix of the collected gel-free semen is drawn and prepared for laboratory analysis. During analysis, the bulk of the semen should be stored in a stabilized incubator which has been preset to the proper temperature (38 degrees C. for equines). As soon as possible, however, the stored semen should be mixed with a pre-warmed life extending blend of chemicals and antibiotics (extender) in preparation for the insemination procedures which should immediately follow completion of the laboratory analysis. If the semen is to be shipped or used at a later time on-premises, the semen-extender mix must be cooled according to a prescribed program as a means of further increasing the sperm longevity. For some species, the semen may be cooled and maintained at refrigerated temperatures (5 degrees C.) for several days allowing safe shipping over long distances. Alternately, some species' semen can be frozen at cryogenic temperatures ($-196$ degrees C.) and stored indefinitely.

The laboratory work must be conducted with great care and be accomplished as rapidly and efficiently as possible. This is necessary to assure good correlation of the laboratory measurements and provide insemination fluid of the highest possible fertility.

The laboratory evaluation of the semen may be quite extensive. However, in routine work a minimal evaluation may be all that is required. A minimal evaluation includes at least the following six measurements and calculations:

1. An initial visual and olfactory examination to appraise semen quality and detect the presence of contaminants (dirt, urine, blood, etc.).
2. A measurement of the total volume of ejaculate.
3. An estimate of semen fertility.
4. A determination of the spermatozoa concentration or density, i.e., the number of sperm cells per unit volume.
5. A calculation of the total number of sperm cells per ejaculation.
6. A determination of the volume of gel-free semen needed for each insemination.

The following additional evaluations are needed for a cooled and shipped and frozen semen programs and are often useful for on-premises breeding programs:

7. A calculation of the number of doses per collection.
8. A recommendation for the volume of extender per dose and the total dose volume.
9. A computation of the dilution ratio.
10. A calculation of the total sperm per dose.
11. A determination of motile sperm concentration.

Items 1 and 2, sensory evaluation and measurement of volume, require no additional comment for purposes of this application.

Item 3, estimation of sperm fertility, is accomplished by a subjective microscopic examination of a standardized dilution of semen to determine the percentage of sperm that are viable. In routine practice, this is done by observing the motility patterns of the spermatozoa and estimating the percentage that move in a typical progressive or forward manner. Other types of movement that have been categorized are circular, vibratory, reverse and flagellating. These latter movement patterns are thought to be indicative of sperm cells that are unlikely to be capable of achieving ovum fertilization. A more detailed evaluation is sometimes used which includes a study of cell morphology under high power magnification. The extent to which the sample is free of cells having certain physical deformities which are thought to affect fertility may be used to refine the fertility rating.

Recently, with ongoing improvements in video and computer technology and the successful marriage of the two, instrumentation has been developed that will make statistically accurate objective measurements of sperm motility. At present, this equipment is used primarily at animal reproduction research facilities. Application at commercial breeding facilities is rare because of the high cost of the equipment compared with that of traditional instrumentation.

Item 4, determination of spermatozoa density or concentration C, may be accomplished by any of the several different methods, four of which are: (1) estimation based upon visual observation of semen turbidity under standardized conditions; (2) visual count using a microscope and hemocytometer; (3) electronic counting; and (4) photoelectric techniques in which a measured optical parameter of a standardized sample is correlated to sperm cell density.

Each method has particular advantages and disadvantages. Visual estimation is rapid and inexpensive but yields the poorest accuracy. Hemocytometer counts can be accurate but are tedious and time consuming. Properly performed electronic counting using modern instrumentation probably provides the highest accuracy but the equipment is expensive and the technique seems better suited to laboratory research and to the gathering of calibration data than to practical field use. Photoelectric instrumentation appears to offer the best compromise when factors of accuracy, rapidity of measurement, required operating expertise, cost and equipment portability are all considered and therefore has received a high degree of acceptance.

Item 5, total sperm per ejaculate Se, is simply the product of ejaculate volume Ve and sperm density C or:

$$Se = Ve \times C \text{ million sperm cells}$$

Where:
  Ve is expressed in milliliters and C in millions of sperm cells per milliliter.

Total sperm per ejaculate may be used as a figure of merit for the male as a breeding animal because it represents his total sperm production capability, especially if it is averaged over a season.

Calculation of the volume of gel-free semen needed for each insemination, Vd, item 6, is done by substituting measured and selected values into a simple equation as follows:

$$Vd = N/(CM))$$

Where:
  Vd is the dose or volume of semen in milliliters (ml) to be used for insemination,
  N is the total number of viable spermatozoa desired for insemination in millions,
  C is the measured concentration or density of sperm in millions of cells per ml, and
  M is the estimated percentage of sperm that are viable (usually percent forward motility) expressed as a decimal fraction.

The total number of viable sperm cells desired for insemination, N, is the minimum number estimated to yield a high probability of achieving ovum fertilization. The selected quantity depends upon the species of animal, any knowledge of the probable degree of fertility of a particular female (from previous experience), and the expertise and judgement of the AI practitioner. As an example, the selected total number of viable sperm cells for insemination of a mare would normally fall within the range of 100 million to 500 million for on-farm breeding programs.

The sperm cell concentration or density, C, and the percent forward motility, M, are both taken from data gathered in the laboratory analysis of the collected semen.

Item 7, the total number of doses per collection Dc, is found from the relationship:

$$Dc = Vc/Vd \text{ doses}$$

Where:
  Vc is the total volume of collected gel-free semen in milliliters and Vd is the volume of gel-free semen per dose in milliliters, computed using the equation of item 6.

The recommended volume of extender per dose, VE, item 8, is based upon field experience and controlled experiments. For on-premises use, a quantity of 10 milliliters of extender is usually specified for equines unless the ratio of extender to semen would be less than 1:1. For cooled shipping the extender is increased to provide a total insemination dose of approximately 40 ml with a minimum dilution ratio of 3:1 (a higher ratio is used for shipped semen to increase sperm longevity). Experimentation with equines, indicates that total dose volumes in excess of 50 milliliters can result in decreased pregnancy rates. Similar considerations, with differing numerical factors, may apply to other animals. Obviously, depending upon sperm concentration and percentage of forward motility, there are situations that will not allow all of the above criteria to be met. In these cases, the judgement of the practitioner (ideally based upon previous experience with the particular animals being bred) is needed to determine the compromise that should be used to optimize the results.

The total volume of the insemination dose Vt, is given by:

$$Vt = Vd + Ve \text{ milliliters}$$

Where:
  Vd is the volume of gel-free semen per dose in milliliters and Ve is the selected volume of extender per dose in milliliters.

The dilution ratio, Dr, verbally defined in the previous paragraph and listed as item 9, may be expressed mathematically as:

$$Dr = Ve/Vd$$

Where:
  Ve is the volume of extender per dose in milliliters and Vd is the volume of gel-free semen per dose in milliliters.

Item 10, represented by Sd, is the total number of spermatozoa per dose without regard to the progressively forward motility. This parameter is particularly useful when working with cooled or frozen shipped semen. Determination of the number of motile cells per dose of semen, as received after shipping, may be found by simply multiplying Sd by the measured percent forward motility of a semen sample taken after the recovery process (proper thawing or warming) has been completed. SD may be found from the relationship:

$$Sd = C \times Vd \text{ million cells}$$

Where:
  C is the measured sperm concentration in millions of cells per milliliter and Vd is the volume of gel-free semen per dose in milliliters.

Motile sperm concentration, Cm, Item 11, is the number of motile sperm per milliliter of dose, determined after the addition of extender. This parameter is also mainly of importance when working with cooled or frozen shipped semen. The motile sperm concentration may be found from the relationship:

$Cm = N/Vt$ million cells per milliliter of dose

Where:
N is the total number of motile cells per dose in millions and Vt is the total volume of semen and extender per dose in milliliters.

A review of the eleven steps required for a minimal evaluation of the collected semen shows that most are simple measurements or calculations or are subjective evaluations. Only two items require or lend themselves to the use of sophisticated instrumentation as a means of improving the rapidity and accuracy of semen evaluation. One of the items, estimation of semen fertility, can be enhanced through the use of a high quality phase-contrast type microscope. The evaluation, of course, remains subjective. Objective fertility ratings can be obtained from automated measurements of forward motility using computerized video equipment if the cost of the apparatus is not considered to be prohibitive. As alluded to earlier, the second item that can be instrumented is the measurement of spermatozoa density. A photoelectric method for estimating sperm concentration in semen was first reported in 1939 by Comstock and Green for the ram.

Several scientific studies have since been made by other investigators to determine the relationship between the sperm concentration of various domestic animals and such photometric parameters as light scattering (or haze), transmission and absorbance. Both duplicate hemacytometer counts and electronic counting have been used to establish the independent variable.

Before measurement, the semen is diluted by a standardized ratio. Various diluents have been used, most consisting of distilled water with a small percentage of sodium citrate or sodium chloride to balance osmotic pressures on the sperm cells. In addition, some investigators have advised the inclusion of formalin to kill and fix the spermatozoa. The standardized ratio of semen to diluent is initially determined by experiment. It is dependent upon the average semen turbidity of the species and the type of instrument to be used. The dilution ratio is chosen to optimize the spread of readings over the usable range of the selected instrument.

The investigations revealed that no photometric parameter could be considered a truly linear function of sperm concentration over the full gamut of densities that might be encountered. However, for several species absorbance was discovered to be tolerably linear over a rather wide practical range of median concentrations, with slope changes being evident usually toward both extremes of the scale. Acceptable accuracy could often be achieved by assuming a linear relationship for a practical range of values followed by smoothing the measurement deviations by using a linear least squares regression analysis to derive a best-fit calibration equation.

A technique that has been devised to provide improved accuracy where needed is to specify two or more dilution ratios with corresponding linear regression equations. In effect, this forms multiple overlapping ranges with a portion of each range falling over the most linear segment of the instrument characteristic. A subjective evaluation of semen turbidity is then used to select the dilution ratio-equation set that will optimize the measurement accuracy.

Another research finding was that the dominant radiation wavelength used for absorbance measurement is not a critical factor, at least over the range of the visible spectrum (380 nm to 760 nm). Absorbance simply decreases in a smooth and fairly gradual manner as wavelength is increased. This indicates that any wavelength of convenience (or even a wide band of wavelengths) may be used providing that measurements are made under the same conditions that were established for calibration of the instrument.

For a number of years, objective measurements of sperm concentration have been successfully accomplished in the field using specially calibrated general purpose laboratory spectrophotometers. Most of the instruments in use are analog types which were primarily designed for measurement of percent transmission of light through test samples at a selected (narrow band) wavelength. The more modern of these instruments include an absorbance scale which is logarithmically related to percent transmission (absorbance equals 2 minus log 10 of the percent transmission). Because a linear transmission scale can usually be interpolated and read more accurately than a non-linear absorbance scale, many of the operating procedures in use are based upon measurement of transmission. Conversion to absorbance is accomplished mathematically by the operator or, more conveniently, may be part of a computerized program if the sperm density value is taken from computer derived graphs or charts showing transmission as the independent variable.

In 1982 an investigation and analysis of commercially available photometers was conducted. None were found to be specialized (or even particularly well suited) for efficient use in the measurement of sperm density. This led to the development of a sperm Densimeter (U.S. Pat. Nos. 4,589,774 and 4,632,562) which has been manufactured for several years by the Animal Reproduction Systems Division of Dupree, Incorporated, assignee of the above referenced patents. This instrument is basically an analog design with digitization of some of the internal functions. It succeeded in providing improved efficiency and accuracy over prior methods of measurement and was well received by the industry. The core features and advantages of the original Densimeter include: A direct digital display of sperm density, thus eliminating the need for reference to charts or graphs; considerable improvement in accuracy through the use of direct absorbance measurement coupled with a three-segment data curve fit, which also eliminated the need for use of multiple dilution ratios; a broad spectrum low power light projection system for improved reliability; an insemination dose computer featuring digital display of the calculated dose, automatic entry of the measured sperm density, and digital thumbwheel entry of both percent forward motility and total viable sperm per dose. The stability of the original Densimeter is good and, although several steps of adjustment and a set of five calibration standards having known absorbance values are required for accurate calibration, the adjustments are independent, non-iterative and seldom required.

It is an object of the present invention to provide an instrument which functions on the basis of a transmittance measurement and which automatically performs zero and full scale transmission measurements for standardization.

It is an additional object of the present invention to provide a new and improved instrument which is microprocessor based and which provides improved reliability, superior accuracy, simplified operating procedure, greater versatility, elimination of manual calibration, and the availability of "expert advice" to aid the practitioner as needed in the decision making process.

It is an object of the invention to provide an instrument for measuring sperm concentration and calculating dose value and having an optical assembly with a light source, a specimen holder and a photodetector, a computation means, a display, and storage means for storing a concentration calculation equation, with the computation means including means for calculating sperm concentration using the stored concentration calibration equation and a sample transmittance value.

A further objective of the invention is to provide an optical assembly having means for measuring transmission of the specimen holder while empty with the light source energized, TFS, sample transmission of the specimen holder with a semen specimen with the light source energized, TS, and dark cell output of the photodetector with the light source energized, DC, with the computation means including means for calculating actual sample percent transmission as follows (TS−TDC)/(TFS−TDC).

An additional object of the invention is to provide an instrument wherein the means for measuring includes means for making a plurality of sample transmission value measurements in sequence and calculating an average for the plurality of sample transmission value measurements. A further object is to provide an instrument having means for providing the concentration calculation equation in the form of a multi-term polynomial derived from a plurality of data points relating measured sperm concentration and measured sperm transmittance value.

Another object of the invention is to provide an instrument wherein the computation means includes means for calculating actual volume of semen to be used as a dose, Vd, as follows $Vd = N/(CN)$, where N is total number of viable spermatozoa desired, C is calculated sperm concentration, and M is estimated percentage of sperm that are viable. A further object is to provide an instrument wherein the light source includes a low power, lens-end light emitting diode producing a beam of narrow-band red light with a dominant wave length of 660 nM collimated with a collimating tube, and with an optically unfiltered silicon photodetector responsive to visible light in the red portion of the spectrum.

Further objects of the invention include calculation of number of insemination doses per collection, recommended volume of extender, total insemination volume, dilution ratio, total sperm dose, and motile sperm concentration and provision of additional calibrations for alternate animals (bulls, boars, rams, endangered species, etc.) and processing protocols (immediate use, cooled shipment, frozen, etc.) to be transferred into the densimeter by connecting the densimeter's serial port to a personal computer and running a loader program. Once loaded, the operator may select any of the new species calibration/processing protocols in addition to the original stallion semen processing protocols.

An additional object is to provide a densimeter with a built in "expert system" which can automatically optimize the number of motile sperm cells, number of insemination doses per collection, recommended volume of extender, total insemination volume, dilution ratio, total sperm per dose, and motile sperm concentration based on selected usage protocol.

Other objects, features and results will more fully appear in the course of the following description and claims.

SUMMARY OF THE INVENTION

An instrument for measuring sperm concentration and calculating dose value and having an optical assembly with a light source, a specimen holder and a photodetector, a computation means, a display, and storage means for storing a concentration calculation equation and a sample transmittance value. The optical assembly includes means for measuring transmission of the specimen holder, while empty, with the light source energized, TFS, sample transmission of the specimen holder with a semen specimen with the light source energized, TS, and dark cell output of the photodetector with the light source unenergized, TDC, with the computation means including means for calculating actual sample percent transmission as follows (TS−TDC)/(TFS−TDC).

BRIEF DESCRIPTION OF THE DRAWINGS

FIG. 5A through 5E is the program flow chart for the instrument of FIG. 2.

DESCRIPTION OF THE PREFERRED EMBODIMENTS

Figure 1:
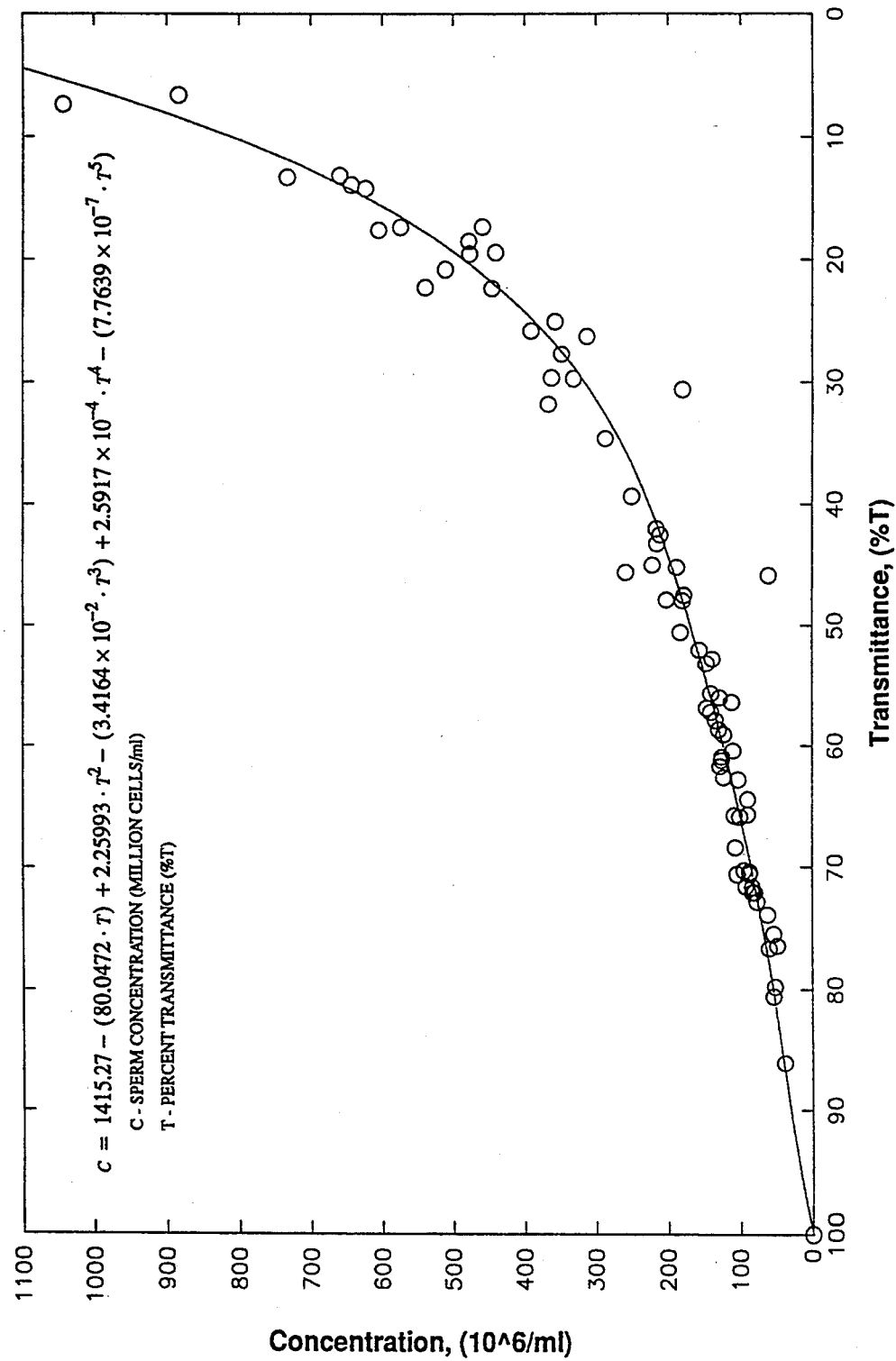
FIG. 1 is a graph showing calibration data with the computer derived calibration equation.

The densimeter of the present invention is a complete redesign of the original densimeter using simplified computer-based methodology rather than analog techniques to provide superior accuracy and enhanced operation. In addition to measuring spermatozoan density and calculating insemination dose volume, the new apparatus calculates and displays total sperm per ejaculate, total number of doses per collection, recommended volume of extender per dose, dilution ratio, total sperm per dose and motile sperm concentration. The new densimeter can store the calibration parameters/protocols of up to twenty species in memory at once. Additional animal calibrations or protocols can be permanently uploaded using a serial communication port. The ability to add new calibrations and calculate additional parameters extends the application of the instrument to alternate stallion semen protocols (cooled-and-shipped, frozen-and-shipped, stored on farm) and other species.

Physically, the system consists of an optical assembly containing a stable light source, a specimen holder, and a photodetector with associated amplifier; a signal converter; a computer with operational programming stored in Read Only Memory (ROM); a port for connection of an external computer and/or printer; and a display and keypad to provide direct two-way communication with the operator.

Operationally, the average photometric transmittance of a diluted semen sample is automatically computed from sequential measurements of full-scale, dark cell, and sample photodetector outputs. These measurements, automatically performed during each cycle, replace the operator adjustments and calibration required in earlier instruments. The computed transmittance value, which is not routinely displayed, is internally entered as the argument of a high order polynomial calibration equation to calculate the sperm density (in millions of sperm cells per milliliter). The calibration equation accurately represents the sperm density of undiluted gel-free semen as a function of the average transmittance of a standard-dilution sample of the semen. The equation was independently derived using sophisticated computer software and is based upon laboratory analysis of a large number of semen samples taken from many different animals of the species. The numerical solution of this equation is stored in memory and presented as SPERM COUNT on a back-lighted alpha-numeric liquid crystal display.

The insemination dose and other additional parameters are automatically computed using equations and logic relationships that are permanently stored in memory. The four independent variables that must be quantified to solve these equations are: The sperm density, measured by the densimeter; the desired number of forwardly motile spermatozoa per dose, selected by the practitioner from experience; the total volume of collected gel-free semen; and percentage spermatozoa forward motility. The latter two are measured in the laboratory using apparatus other than the densimeter. The numerical values of the latter three parameters, expressed in the units of measure designated on an interrogating screen display, are entered into the densimeter via the keypad on the front panel.

The new densimeter includes a RS232C communications port which provides a direct connection to a personal computer or serial printer. When connected to a personal computer, stallion data can be stored into a computer database and alternate animal calibrations can be permanently uploaded into the densimeter. A serial printer can be connected to the RS232C port to produce standard Semen Evaluation Reports and hard copy listings of the measured, selected and computed parameters.

Comparison of New Apparatus with Original Model

Changing requirements within the equine industry (the addition of cooled shipment and frozen storage protocols) and the emerging demand from breeders in other species, created the need for substantial modifications of the original Densimeter. To facilitate the desired changes, a microprocessor based design was chosen due to its inherent flexibility. The benefits of redesign are many, the most significant being improved reliability, superior accuracy, simplified operating procedure, greater versatility, elimination of manual calibration, and the availability of "expert advice" to aid the practitioner as needed in the decision making process.

The prior densimeter and the new present invention are both classified as photometric instruments. Although the fundamental design objective in both cases was to make significant improvement on the existing "best system", the techniques and means of achieving improvement are quite different. The major detailed design goals for the new instrument are synonymous with the "benefits of redesign" enumerated in the previous paragraph. In addition to these goals, it is desirable for the new densimeter to be capable of interfacing with personal computers for data storage and report generating. Considerable effort was expended in simplifying the physical construction of the new apparatus to improve manufacturing efficiency, reduce overall production costs and aid in achievement of the technical design goals.

Light Projector

Both systems require a source of projected light. Standard spectrophotometers provide narrow band (10 nM) light having a wavelength which is selected by an adjustable optical grating. This requires a high power lamp with resulting short operating life and, in some instruments, a need for re-calibration with each lamp replacement. Research data shows that the absorbance or transmittance of dilute semen changes very little with wavelength in the visible spectrum. Because of this, the expensive optical grating may be eliminated. Visible light of any wavelength or even broad spectrum light may be used provided that the calibration data and measurement data are obtained with identical systems. The earlier densimeter used broad spectrum light from an incandescent lamp, an aspheric lens to efficiently gather and focus the light, and a photopically filtered photodetector to block reception of infrared energy. This reduced the projection lamp power requirement from the 100 to 150 watts required for conventional spectrophotometers to approximately 2 watts, and greatly improved lamp stability and reliability.

Advances in light emitting diode (LED) technology now make high efficiency, high intensity lamps available at low cost. Almost all LED's include some type of molded plastic lens to shape the distribution of emitted light into one of several desirable patterns. The new densimeter uses a lens-end LED which emits a broadly focused beam of red light (having inherently narrow band width and a dominant wavelength of 660 nM) that radiates insignificant levels of extraneous infrared energy. This allows the use of an optically unfiltered silicon photodetector which has a high responsivity to visible light in the red portion of the spectrum. Experiments indicated that the required sharply defined beam of light could be obtained by outfitting the LED with a collimating tube rather than using an expensive auxiliary lens. It was also found, because of the improved sensitivity of the optically unfiltered photodetector and the high energy conversion efficiency of the LED, that more than sufficient beam intensity could be achieved with an LED current of only 25 milliamperes. This equates to an input power of approximately 45 milliwatts, about 2% of the lamp power used by the original densimeter and less than 0.045% of the power used by a standard spectrophotometer.

Because of it's intrinsic long life, mechanical ruggedness and low power requirement, the use of an LED as a projection lamp is a significant improvement in instrument reliability. The LED projection lamp and associated lamp current regulator used in the new densimeter should operate virtually trouble-free over the entire life of the instrument.

Signal Processing

The earlier densimeter used absorbance measurement of the dilute semen sample as a first step for development of a more nearly linear and direct relationship between sperm density and its electrical analog. This was followed by automatic three-segment linear curve fitting for improved accuracy at low and high density counts. Calibration was achieved using a bank of potentiometers to trim the output into an accurate signal for the digital panel meter Sperm Density display. The calibration data was based upon photopically corrected "white light" absorbance measurements recorded with the associated sperm density measurements obtained by electronic counter or other means.

The Dose Computer of the original densimeter was an analog design which used a digital technique for automatic entry of sperm density and digitally marked thumbwheel panel switches (which produce analog outputs) for input of total motile sperm per dose and percent forward motility. The dose figure was read on the digital panel meter.

The New Instrument

The new computerized densimeter operates in transmission mode which is an inverse complex exponential function of sperm density. Transmission measurements require calibration for both zero and full scale photodetector output rather than zero alone as needed in absorbance measurements. This disadvantage is overcome by the instrument's internal microcomputer which automatically performs both adjustments in less time than the single manual adjustment required in the original system. An advantage of transmission over absorbance measurement is the elimination of the expensive temperature-compensated log amplifier (with its small attendant errors) used to produce the absorbance output in the earlier instrument. A second advantage of this measurement method is the elimination of all manual calibration procedures required by the original densimeter.

To form a basis for calibration, the new system requires that the "red light" (660 nM) transmittance of many standard dilution semen samples, taken from a statistically relevant number of males, be measured and recorded along with the corresponding sperm density measurements made by electronic counting or by manual procedures using a microscope and hemocytometer. The data points are smoothed to average any measurement anomalies and reduced to the form of an equation using computer software specifically designed for curve fitting applications. In the case of equines, a sixth order equation is required to accurately represent sperm density as a function of standard-dilution semen transmittance. An example of a calibration equation with the corresponding graph showing the collected data points is presented in FIG. 1. The equation is permanently stored in memory and represents the instrument calibration in a form that cannot drift with time or temperature.

The new densimeter determines sperm density by first measuring the transmission of a clear diluent filled cuvette during the "Zeroing" phase. This measurement is used as the full scale transmission reference. The densimeter display requests that the cuvette, filled with diluent, be placed in the specimen drawer prior to this measurement. Next, the instrument display requests that the operator remove the cuvette from the specimen drawer, add a specified amount of semen, and replace the cuvette in the drawer. The new densimeter then measures the diluted sample transmittance by taking multiple readings which are averaged over a fifteen second period. The lamp is then automatically turned off and a dark cell measurement is taken. These three parameters (Full Scale Transmission, Sample Transmission and dark cell output) are used to calculate the actual sample transmission percentage. This is done by dividing the Full Scale Transmission minus dark cell output into the Sample Transmission minus dark cell output. The ability of the densimeter computer to automatically take these three readings for evaluation of each semen sample replaces the need for field calibrations performed by the operator. Once the actual sample transmission percentage is calculated it is automatically entered as the argument into the calibration equation and the numerical solution of the equation in millions of sperm cells per milliliter is presented in large easily read characters on the instrument display.

The functions of the original analog dose computer have been completely incorporated into the new densimeter's microcomputer. The microcomputer expands the ability of the densimeter to calculate multiple parameters (six for equines) in addition to semen dose. The technique is similar to that used with a programmable calculator. The equations and decision making logic are stored in non-volatile Read Only Memory (ROM). Numerical values for a set of the required independent variables are selected or measured and entered on a front panel keypad by the practitioner. Solutions to these equations are calculated and immediately displayed following data entry. The equation parameters may be changed to satisfy the needs of the various different females to be bred with the same semen collection, or to determine the effects of changing certain parameters if compromise is required. The measuring steps and the calculations can be performed manually if desired.

Front Panel

Figure 2:
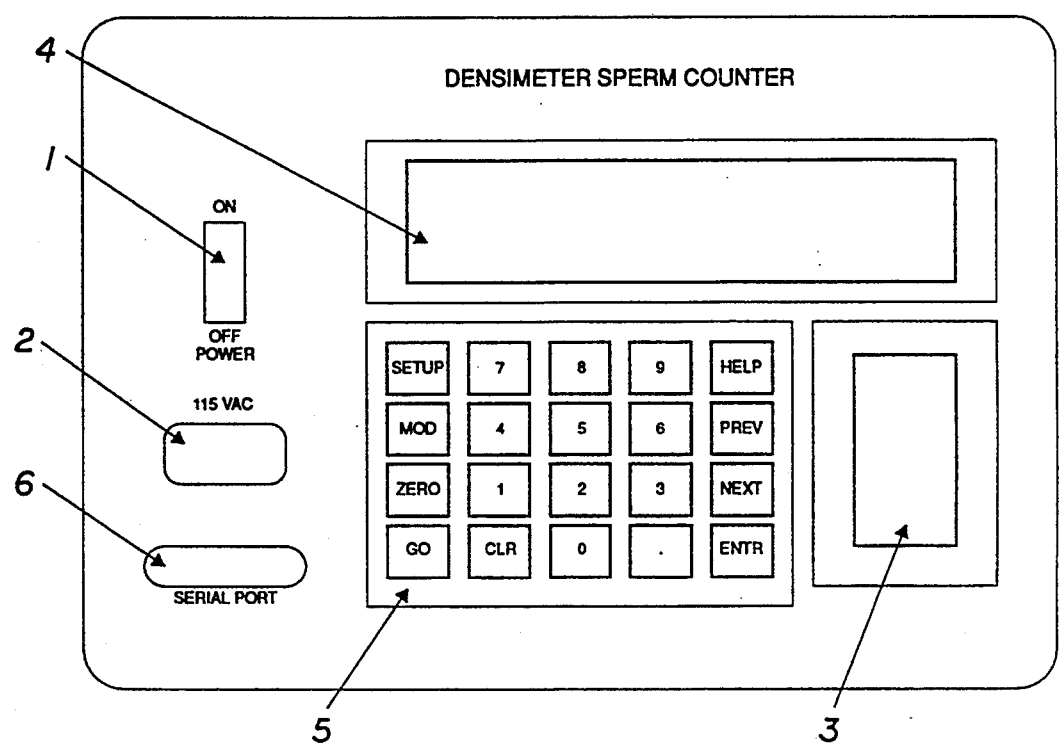
FIG. 2 is a front view of a densimeter incorporating the presently preferred embodiment of the invention.
Figure 3A:
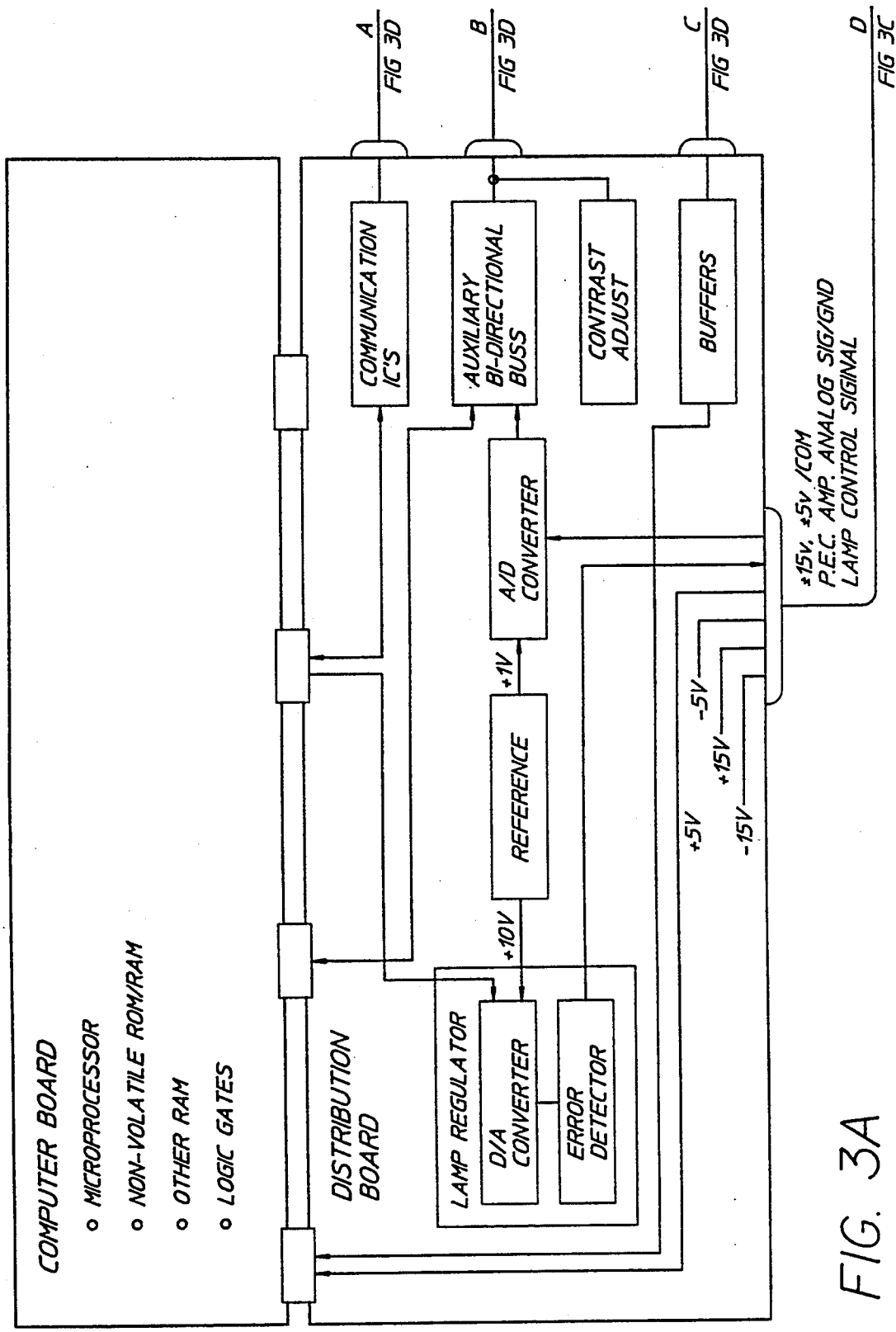
FIGS. 3A through 3D are an electrical block diagram of the instrument of FIG. 2.
Figure 3B:
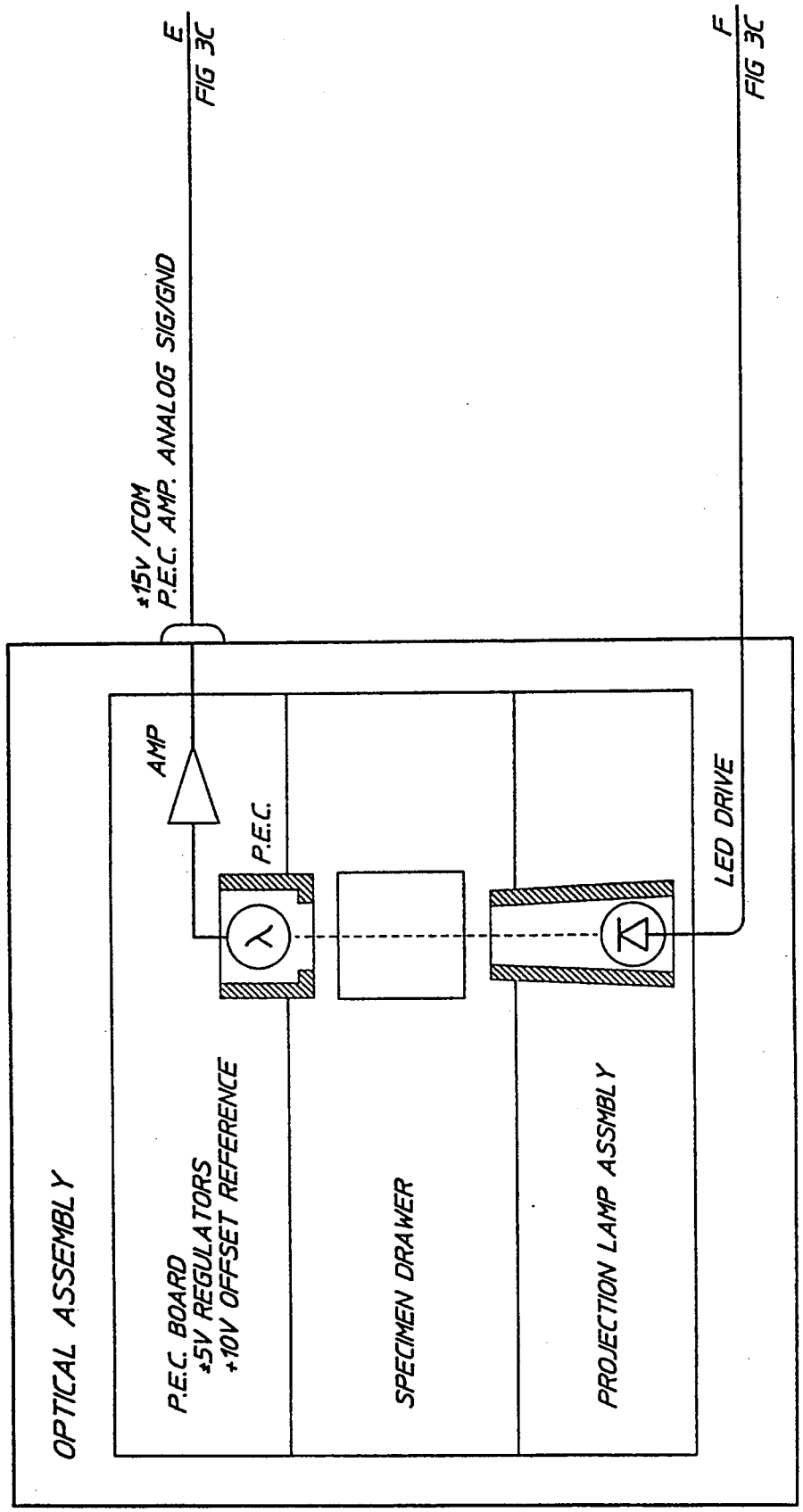
Figure 3C:
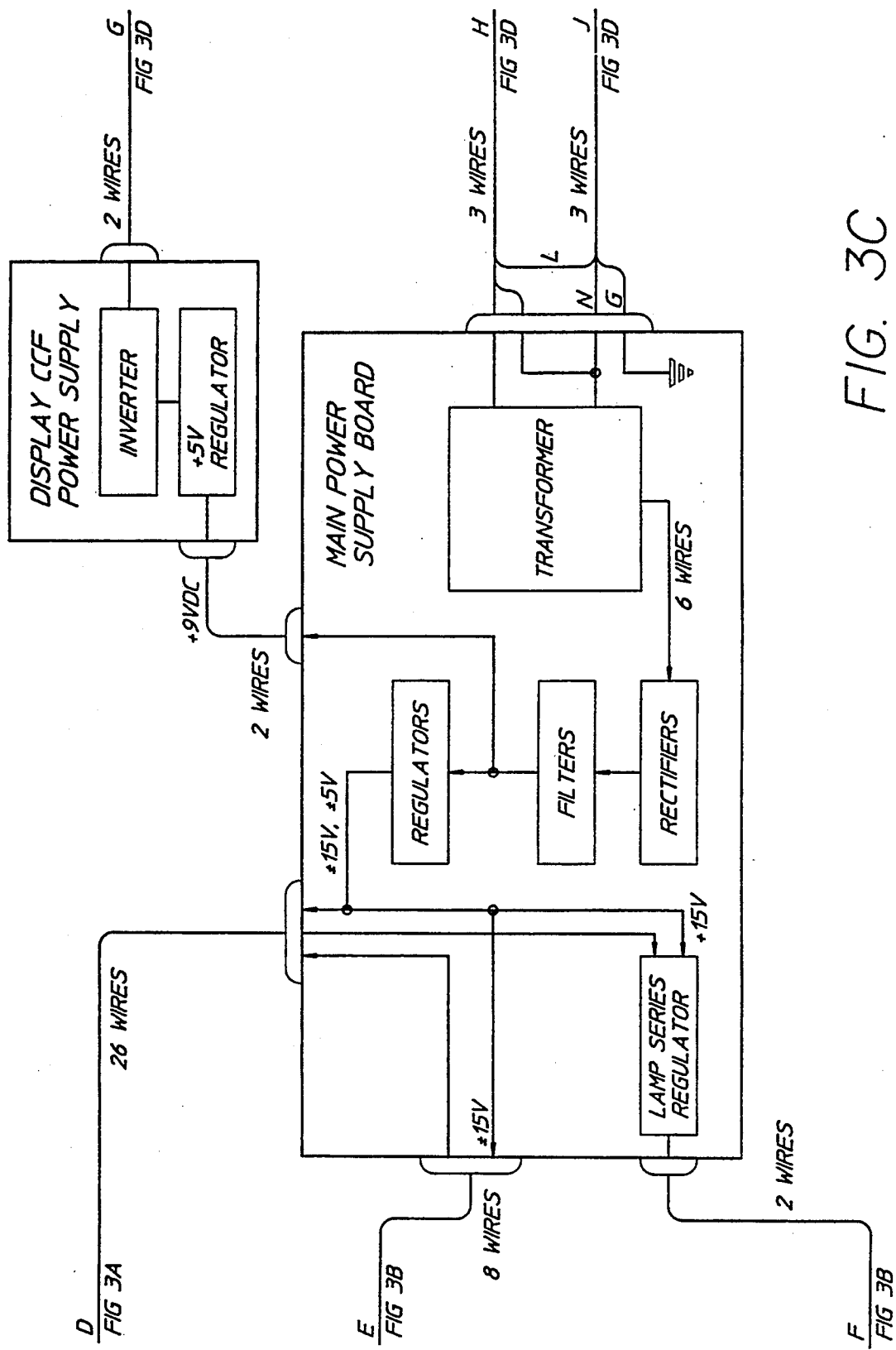
Figure 3D:
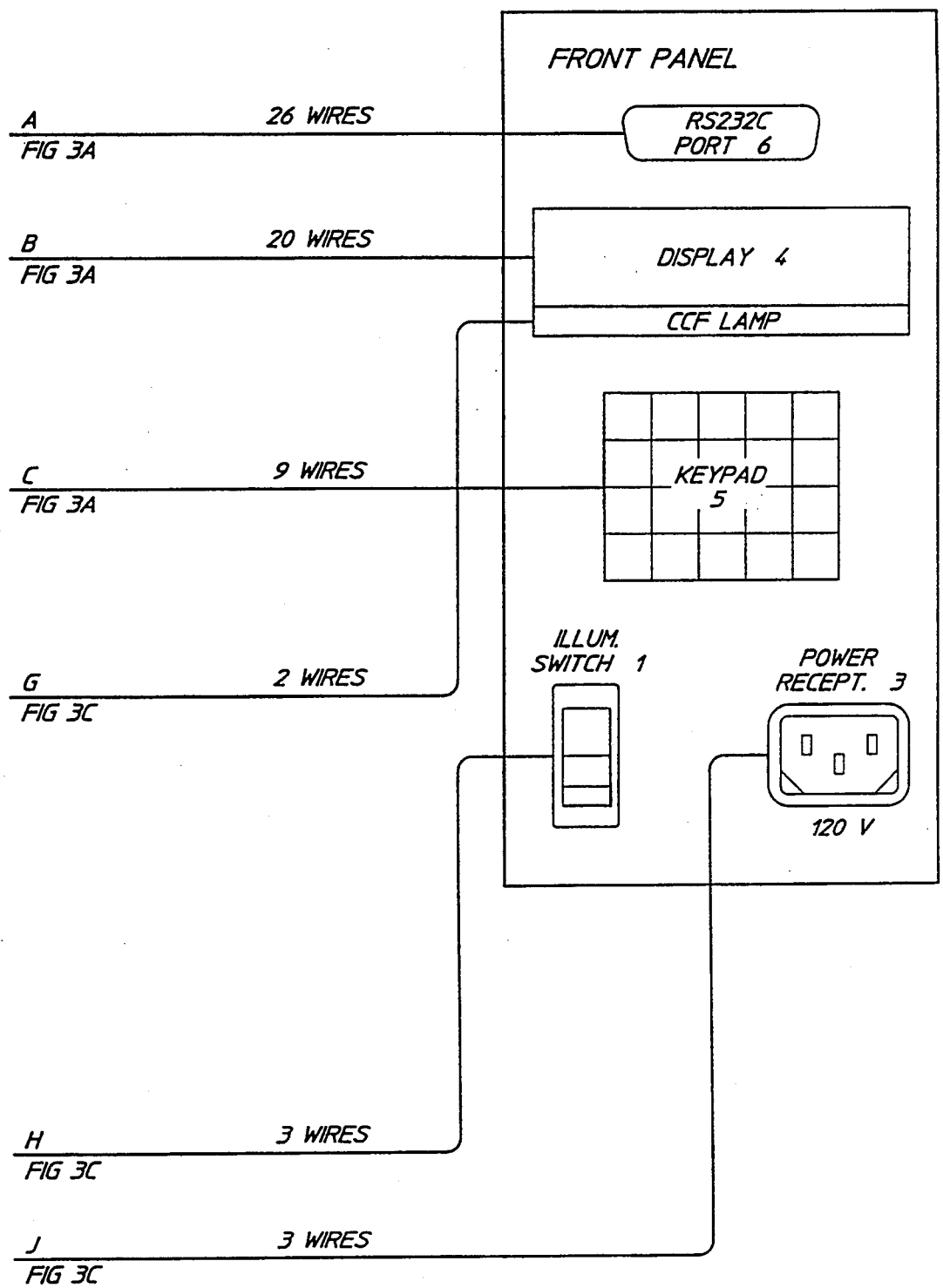

The front panel, shown in FIG. 2, includes an illuminated power switch 1; a power cord receptacle 2; a specimen drawer 3; an illuminated 1.5"×5" 40 character by 8 line with graphics LCD display 4; a 20 button key pad for program selection and entry of data and commands 5; and a serial communications port for connection of a computer or serial printer 6.

Block Diagram

The block diagram, FIGS. 3A through 3D, identify the electronic sub-systems that comprise the instrument. The major elements and their interrelationships are described in the following paragraphs.

Power Supply

The main Power Supply Board is of entirely conventional design. Briefly, a 50/60 Hz power transformer having a universal 120/240 VAC primary winding is used to provide line isolation and supply appropriate AC potentials for the development of $+/-15$ VDC and $+/-5$ VDC outputs.

One center-tapped secondary winding drives a dual diode rectifier with capacitive input filter, followed by a 3-terminal integrated circuit (IC) voltage regulator, to produce $+5$ volts at up to 700 milliamperes (ma) for the microprocessor and associated digital circuitry. The DC potential at the regulator input (approximately 9 volts) also supplies power at 300 ma to the LCD display back-light inverter.

The other secondary winding, also center-tapped, drives a bridge rectifier and two input filter capacitors to develop bipolar DC potentials which are regulated to $+15$ and $-15$ volts by a pair of 3-terminal IC voltage regulators. These potentials are used primarily by low power linear amplifiers in the instrumentation circuitry. The $+15$ volt line also supplies input power to the projection lamp (LED) programmable current series regulator transistor while the $-15$ volt line additionally provides input to a small IC voltage regulator which reduces the potential to −5 volts needed by a bipolar input A/D converter.

The remaining on-board components such as line fuse, line transient suppressor, by-pass capacitors, regulator protection diodes and heat sinks are obvious in purpose and are not shown at the block diagram level.

Other boards, to be described, also contain elements related to the power supply such as precision voltage references for instrumentation sub-systems (D/A converters, etc.) or small on-board regulators to provide isolation or additional immunity from the effects of load current or line voltage changes.

Computer

The microcomputer is located entirely on the Computer Board and was designed for a broad range of products and applications. Modifications for alternate applications are achieved by making simple hardware changes combined with product-specific software. Unused memory and input/output chips can be simply removed if not needed for a particular design jumpers on the Computer Board allow the selection and activation of a hardware real-time clock and several external interrupts. The 8-bit HMOS microprocessor has a clock rate of approximately 5 MHz. As customized for the densimeter, the microcomputer is configured with 32K of EPROM, 8K of non-volatile RAM, 1K of other RAM and a real-time clock. The entire board operates from a single +5 volt input which is provided by the main Power Supply Board.

Distribution Board

The Distribution Board acts as the main signal distribution link between the computer and the peripheral boards in the Densimeter. This board contains the master voltage reference for the system, keyboard/display buffers, auxiliary bi-directional computer buss, serial communications hardware, and the signal processing converters to measure the photocell output and adjust lamp intensity. The computer board is mounted to the distribution board in a "piggyback" configuration using board-to-board connectors. The other peripheral boards; display, photoelectric cell, power supply, and RS232C interface, are connected to the distribution board via ribbon cable connectors.

Key Pad

The 20 button Keypad 5 is a purchased item which provides the user with good tactile feedback. The buttons, having customized indicia as shown, are used to select programs, enter commands or enter numerical data in response to on-screen requestors. The meaning and use of the various specially marked keys will be covered in the Detailed Operating Procedure. Electrically, the Keypad consists of a 20-contact multiplexed 4×5 matrix. A 9-wire ribbon cable connects the Keypad to the Distribution Board where the buffers and associated pull-up resistors are located. Keypad connection from the Distribution Board to the Computer Board is by a direct board-to-board connector.

Alpha-Numeric Liquid Crystal Display

The large (1.5×"5") back-lighted liquid crystal Display 4 located on the front panel, can present 8 lines of alpha-numeric information with up to 40 characters per line. The display is a graphics type having a resolution of 240'64 pixels that can be addressed, using bit map techniques, to present block or line art or oversized characters. With more sophisticated programming, it is possible to produce simple moving pattern effects, such as a "neighing horse" logo which is shown momentarily when the densimeter is first energized. The purchased unit includes a display driver and the logic required to generate standard alpha-numeric symbols from a conventional 7-bit binary ASCII input. The display is connected by a 20-wire ribbon cable to the Distribution Board where it is routed to an auxiliary bidirectional buss shared with an A/D converter and another connector shared with the keypad. The display contrast may be optimized by adjusting a buffered potentiometer which is also located on the Distribution Board.

The display includes an integral cold cathode fluorescent (CCF) tube, which injects light evenly along the top edge of the display, and a back reflector to produce a uniform brightness level over the entire surface of the display.

Display Back-Light CCF Power Supply

The display back-light Power Supply is a separate purchased unit specifically designed to operate the cold cathode fluorescent tube used for display illumination. The power supply is a miniature inverter that initially produces a high voltage AC output to cause ionization of the fluorescent tube gas, then shifts into current mode regulation to maintain constant light output at the desired brightness level. The inverter requires a +5 volt DC input at 300 ma which is provided by a dedicated on-board IC voltage regulator. Input to the regulator is taken from the +9 volt filtered rectifier output which feeds the +5 volt system regulator located on the main Power Supply Board.

Optical Assembly

Figure 4:
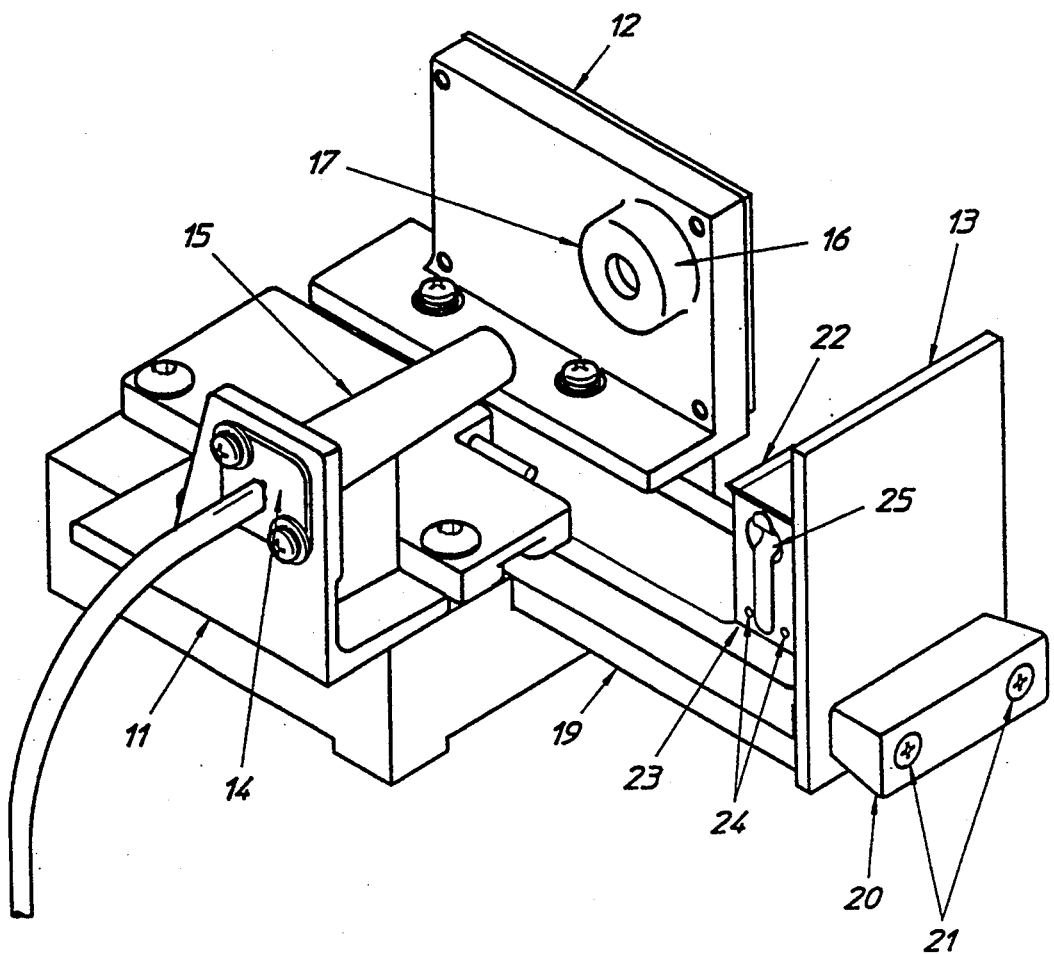
FIG. 4 is a perspective view of the optical assembly and specimen drawer of FIG. 2.
Figure 5A:
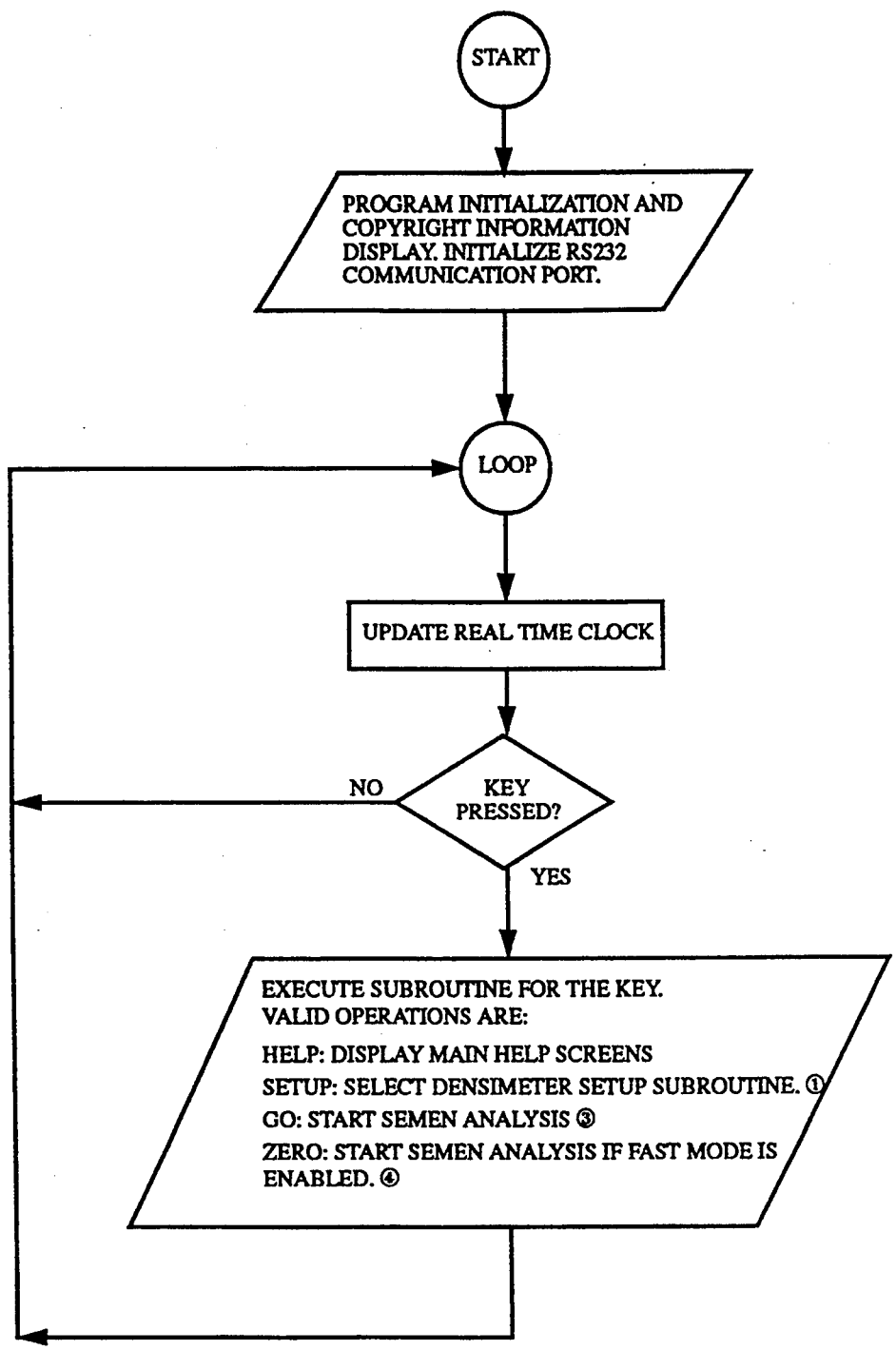
Figure 5B:
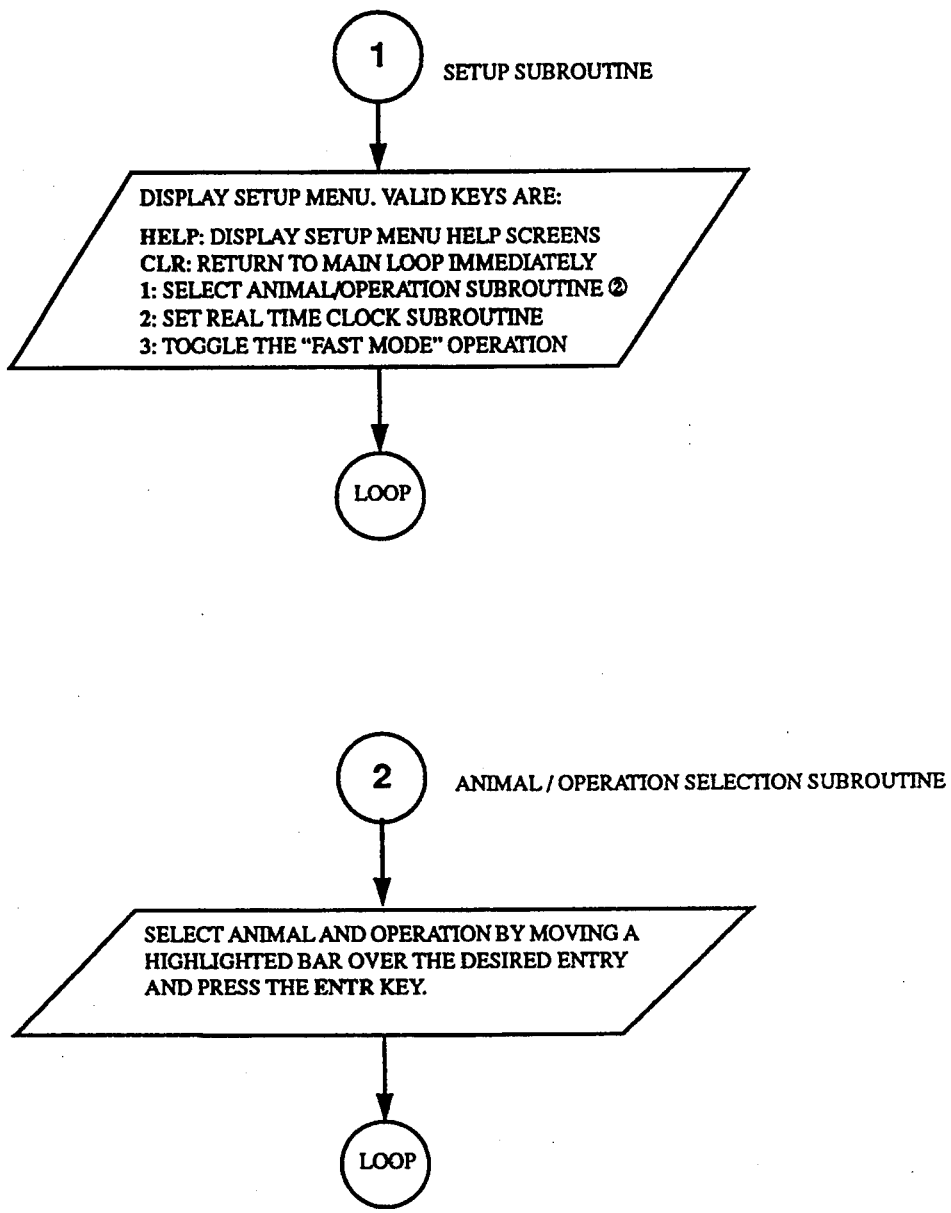
Figure 5D:
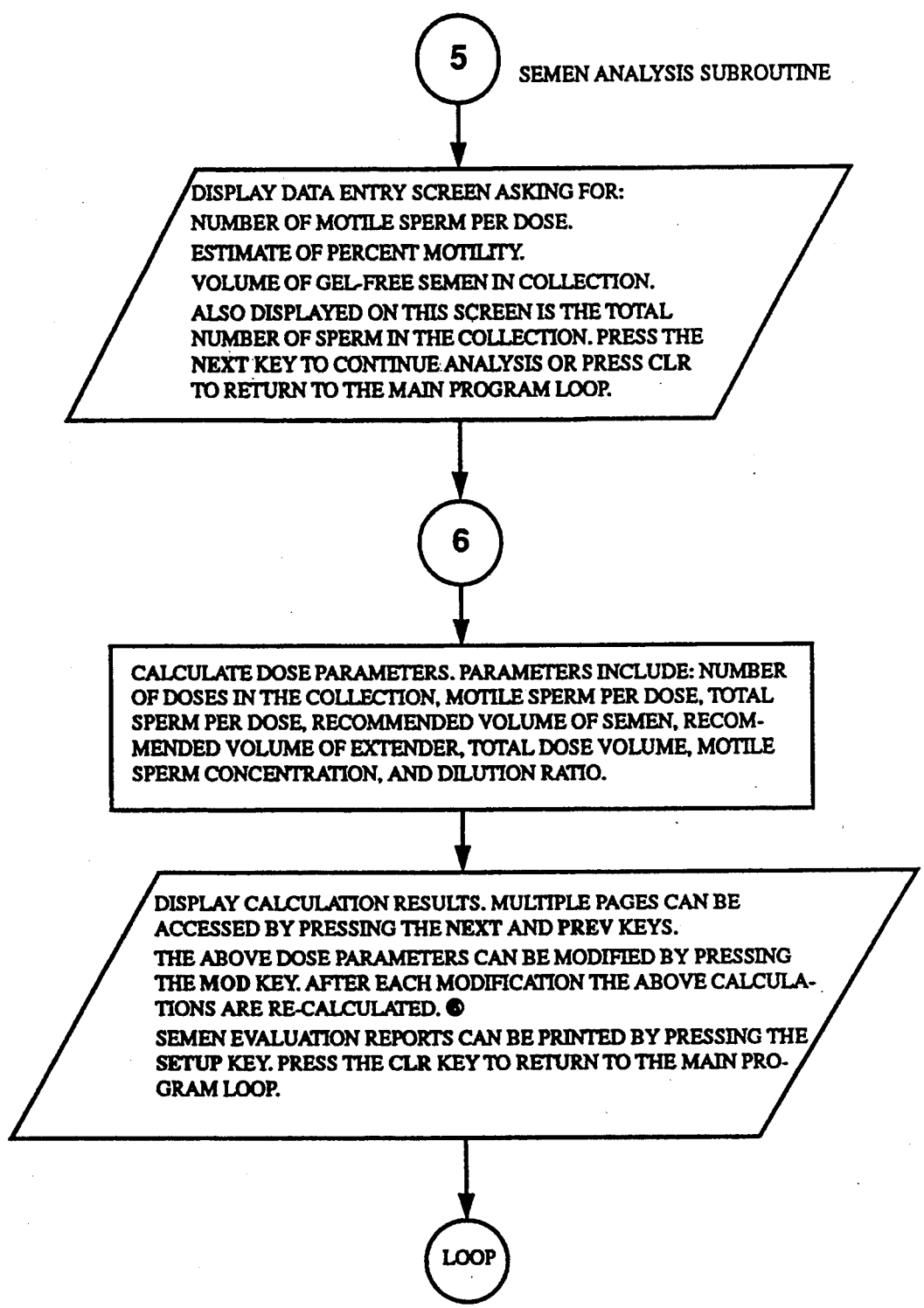
Figure 5E:
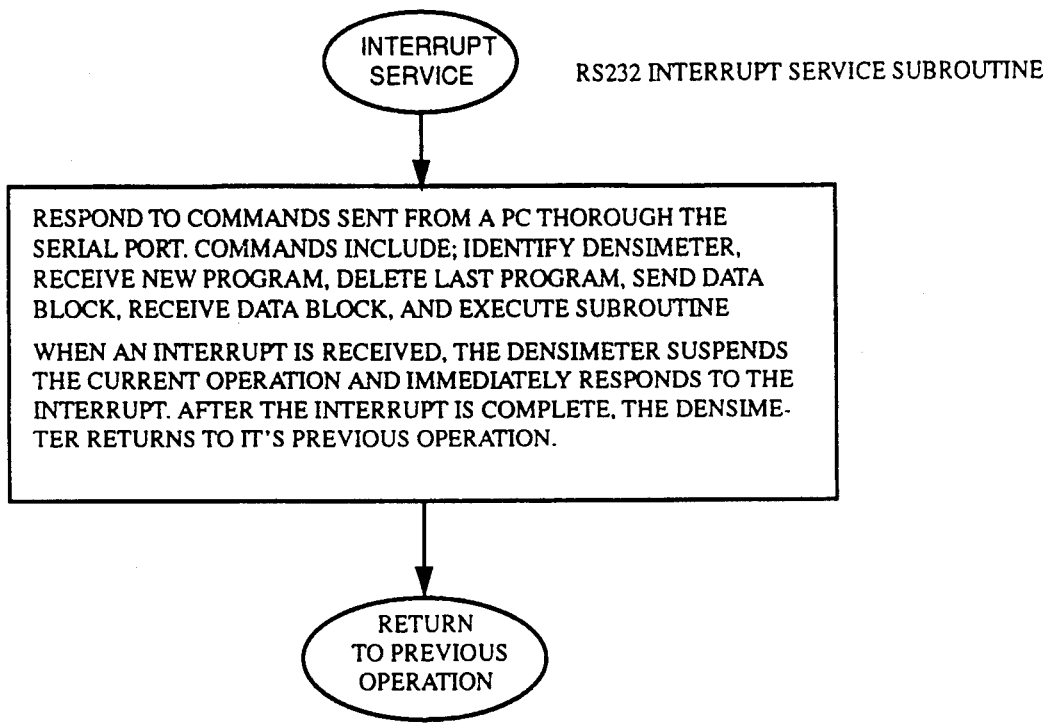

The Optical Assembly, shown in block diagram form in FIG. 3 and physically in FIG. 4, includes a projection lamp/collimating tube sub-assembly 11, a silicon photodetector/amplifier printed circuit board sub-assembly 12, and a specimen drawer/cuvette holder sub-assembly 13.

The projection lamp/collimating tube assembly 11 produces an essentially collimated beam of red light having a dominant wavelength of 660 nM, a half-intensity band width of 30 nM, a beam intensity of approximately 50 millicandelas and a cross sectional diameter of 0.2 inch. The light source 14 is an "extra super bright" LED with integral water-clear plastic lens. The collimating tube 15 is of molded black plastic, 2" in length and slightly tapered with an exit aperture ID of 0.2". The inner surface of the tube is coated with a durable light absorbing matt-black paint to prevent internal reflections from causing beam spreading.

A silicon photodetector 16 is mounted on a printed board 12 behind a shroud 17. The photodetector is selected to meet a number of requirements. The active surface area of the photocell should be circular with a diameter of about 0.25", somewhat larger than the projected light beam diameter. Blue enhancement is not required because the dominant wavelength of the light beam is red. The dark cell impedance should be at least 10 megohms, preferably 25 megohms or more to assure stable photodetector amplifier offset under dark cell conditions. Responsivity is not critical and may be in the typical range of 0.25 to 0.3 amps per watt at 660 nM. The silicon chip is mounted in a 0.5" diameter hermetically sealed metal case having a clear glass window. The photodetector shroud 17 is of molded black plastic and has a circular opening 0.25" in diameter. The photodetector 16 is mounted so that the active surface is 0.5" behind the front surface of the shroud. The main purpose of the shroud is to control the viewing angle of the photodetector. The associated photodetector amplifier also located on printed circuit board 12 will be described in a later paragraph.

Mechanically, the specimen drawer/cuvette holder sub-assembly 13 includes a bottom plate 19 with a front and handle 20, attached to the bottom plate by screws 21. The cuvette holder 22 is attached to a support post on the base 23 by rivets 24. Two springs 25 are provided in the holder to snugly hold the cuvette in a fixed and repeatable position. Appropriate guides and latches may be provided on the drawer as desired. The assembly is so designed that, with the drawer latched in the closed position, no extraneous light reaches the photodetector, and the projected light beam passes through the horizontal center of the cuvette, and with the vertical center axis of the cuvette midway between the exit port of the light collimating tube and the front surface of the photodetector shroud.

In operation, the collimated light beam impinges upon the active surface of the silicon photodetector after passing through the specimen cuvette and the photodetector shroud. The beam remains sharply defined when clear diluting fluid is in the cuvette and fills virtually all of the photodetector active surface area.

The silicon photodetector is operated essentially on short circuit and at a maximum current level which is a small percentage of its saturation current level. Under these conditions, the current is a linear function of the intensity of the total light flux reaching the photodetector. When a standard quantity of gel-free semen is uniformly mixed with a measured volume of diluent in the specimen cuvette, the mixture becomes turbid to a degree dependent upon the sperm concentration. This reduces the amount of light reaching the photodetector and causes a corresponding reduction in the photodetector output current. With appropriate calibration and standardization of measurement conditions and procedures, proper processing of this change in photodetector current will yield an accurate measurement of the sperm density in millions of sperm cells per milliliter.

It is important to note that when photoelectric measurements of transmittance or absorbance are made, considerably greater differences in the measured value will occur between instruments of various designs when measuring a turbid or translucent medium than when measuring a medium that produces little or no scattering of light. When light scatter occurs, instruments allowing a large amount of scatter to reach the photodetector will show smaller changes in output current than those having a photodetector with a more limited viewing angle. The factors affecting photodetector viewing angle are physical spacing between specimen and photodetector, photodetector surface area, physical position of the photodetector shroud, and the size of the shroud aperture.

Projection Lamp Regulator

The precision projection Lamp Regulator, located on the Distribution Board (see FIG. 3A), allows the densimeter computer to change the intensity of the projection lamp by adjusting the lamp current. The lamp current must be constant, i.e., completely independent from the effects of line voltage changes and environmental influences for the short duration of the transmittance measurement because the light intensity is not dynamically monitored and controlled during the measurement cycle.

The current regulator consists of a precision op-amp error detector, which compares the voltage drop across a temperature-stable current sensing resistor, connected in series with the projection lamp, to a computer-controlled reference voltage delivered from a D/A converter. The output of the error amplifier sets the bias on a small power transistor, also connected in series with the lamp and fed from the main +15 volt regulated power supply. The error detector maintains equality between the reference voltage and the voltage drop across the current sensing resistor, thereby maintaining the lamp current at the computer selected value. The range of reference potential supplied by the D/A converter is 0 to 10 volts in 255 steps. The resistance values in the regulator circuit are so chosen for this to produce a lamp current range of just a few microamperes, set by a bias which increases the adjustment resolution by overcoming the intrinsic volt drop of the LED, to 25 milliamperes, in steps of 100 microamperes.

The 8-bit D/A converter, which supplies the current regulator reference voltage, is a digitally switched resistance ladder type which in turn requires a reference. This is supplied by a precision temperature compensated master 10 volt reference, also located on the Distribution Board. The reference output is connected to the converter reference pin through a 5K ohm resistor to deliver a constant reference current of 2 milliamperes. The negative output current from the D/A converter resistance ladder, which has a value determined by the digital input to the converter, is changed to a positive output potential by an outboard IC op-amp configured as a trans-impedance inverter. All of the resistors that are required outboard of the D/A converter are precision metal film types having very low temperature coefficient of resistance. The op-amp is a precision type which has excellent temperature stability. By-pass and compensating capacitors are provided as needed and the regulated 15 volt bipolar operating potentials for the D/A converter and associated amplifiers are taken from the main Power Supply Board.

Photodetector Amplifier

The Photodetector Amplifier is located on the photoelectric cell printed circuit board 12 which is part of the optical assembly of FIG. 4. The amplifier is an instrumentation op-amp having low noise, low temperature-stable bias current, low offset voltage, and very high open-loop gain. The circuit is configured as a trans-impedance amplifier or current-to-voltage converter. The photodetector positive terminal (+) is connected to ground and the negative terminal (−) to the amplifier summing junction, which is virtually at ground potential. This configuration causes the photodetector to be essentially operating on short circuit with the output voltage of the amplifier being linearly proportional to the photodetector current. The feedback network has a long time constant (0.1 second) to average the effects of beam modulation caused by small fluctuations of turbidity which occur when the diluted semen is in the cuvette. This is enhanced at a later point in signal processing through the use of long period digital averaging techniques. The amplifier dark cell output is offset by approximately −2 volts to allow the full resolution of the bipolar input A/D converter to be utilized. Automatic program-controlled adjustment of the projection lamp brightness sets the full scale (100% transmission) amplifier output to approximately +2 volts yielding a nominal amplifier output voltage change of 4 volts for zero to 100% transmission. This improves accuracy by doubling the digital resolution of the percent transmission signals. The amplifier offset bias current is provided by an on-board +10 volt temperature stable IC voltage reference which is coupled to the amplifier summing junction through a low temperature coefficient resistor of appropriate value. Op-amp supply potentials of +/−5 volts are produced by a pair of on-board IC voltage regulators and separate signal and power supply grounds are provided to improve accuracy and maximize the immunity of the amplifier to power line voltage variations. The voltage reference and on-board regulators are fed from the regulated bipolar 15 volt potentials provided by the main power supply board.

Signal Converter

The photodetector amplifier output provides all of the signals required to determine both sperm count and projection lamp intensity. The significance and use of the amplifier output potential is determined by the densimeter microcomputer programming in conjunctions with the operators' keypad inputs. The first step required in processing the photodetector amplifier output is to change the analog signal to digital format. This is accomplished by a monolithic 5½ digit A/D Converter which is located on the Distribution Board. The Converter uses a modified dual slope technique to provide a bipolar resolution of 400,000 counts. It is designed for microprocessor interface and features software selectable interface modes and baud rates. A full scale linearity of one count (typical) is achieved through external computer correction techniques. The analog section has a true differential input designed for (+) or (−) inputs and includes a very effective auto zero system. The frequency of the clock crystal is selected to minimize sensitivity to 50/60 Hz power line interference and the outboard integrating circuit resistor and capacitor are chosen to optimize the voltage swing and basic linearity of the converter. The 1 volt reference required to establish a full scale sensitivity of 2 volts is derived from a precision temperature stable 10:1 voltage divider connected to the output of the master 10 volt reference. The digital output of the A/D converter is directed to the computer through the auxiliary bi-directional buss which it shares with the display.

Communications System

The serial communications port 6, is a standard 25-pin RS232C connector located on the front panel of the densimeter. This connector is connected to the Distribution Board where the associated circuit components and IC's are located. The serial input and output transmissions are converted between RS232C and TTL levels by an RS232C communications integrated circuit. The communication port is electrically isolated from the rest of the densimeter by opto-isolators on the input, output and ground connections. The system is powered by the regulated +5 volt potential provided by the main Power Supply Board.

Densimeter Operation/Program Flow Chart

The operation of the densimeter of the present invention is controlled by the main program which is stored in two 8K byte read only memory (ROM) chips on the computer board. FIGS. 5A through 5E are program flow charts of all major operations and procedures. The main program includes processing protocols for stallion semen to be used immediately (IMMEDIATE USE), and for cooled stored/transported (COOLED AND SHIPPED) semen. Additional animal calibrations (other species) and/or protocols can be loaded into an 8K byte nonvolatile random access memory (NVRAM) chip which is also located on the computer board. Additional calibrations are permanently loaded into the Densimeter by connecting the serial port to a personal computer and uploading the new calibration from a floppy disk. Once loaded, the new calibration or protocol is added to the list of choices the operator may select.

To select a different calibration/protocol, the operator follows simple on-screen instructions and scrolls through a list of available options. When the desired selection is highlighted, the operator presses the enter ENTR key and the new calibration/protocol is selected. The densimeter will automatically remember the last calibration/protocol used from session to session so that the operator only changes it when necessary.

To start a semen analysis, the operator presses the GO key and follows the instructions shown on the screen. The first step in the analysis process is to set and measure the full scale output of the photodetector. This is done by instructing the operator to place a new cuvette into the sample drawer filled with clear diluent and pressing the enter key. The lamp intensity is adjusted until the photodetector amplifier output is between 1.8 and 2.0 volts. This measurement is recorded into the memory, for later use.

The next step in the semen analysis process is to measure the transmission through the semen/diluent mixture. A screen prompt requests the operator remove the diluent filled cuvette from the sample drawer and add a measured amount of semen to the cuvette. The transmission of the semen/diluent mixture is computed by averaging multiple photocell measurements over a 15 second period. This multiple measurement technique is necessary to provide a better estimate of the average transmission of the sample. At the end of the 15 second measurement, the Densimeter turns the lamp off and measures the dark cell transmission (the output of the photocell with no illumination).

The final step in determining the sample percent transmission is to perform the calculation using the three parameters, full scale, sample, and dark cell transmission. The percent transmission can be calculated by the following equation:

$$PTs = \frac{TS - TDC}{TFS - TDC}$$

Where:
PTs = Percent transmission of the sample.
TS = Sample transmission.
TDC = Dark cell transmission.
TFS = Full scale transmission.

The densimeter uses the calculated percent transmission as the independent variable in a multi-term equation which represents the sperm density. The sample transmission percentage is not normally displayed but is used internally. The resulting sperm density, in units of millions of sperm per milliliter of gel-free semen, is displayed in large 0.5" high easily read numbers.

The next step in the semen evaluation process is to enter, via the keypad, the total gel-free volume of semen collected, desired motile sperm per dose, and the estimated motility factor. The Total sperm in the ejaculate is automatically calculated and displayed on this screen after the total gel-free volume is entered. Once these factors are entered, the operator is presented with a calculation screen with the various important parameters for the dose displayed. The initial values of the parameters represent the built-in "expert systems" recommendations for the insemination dose. The parameters can now be customized by an experienced operator as desired. When a parameter is modified, all other parameters are re-calculated to reflect the modification. The exact parameters will be different based on the animal or protocol selected.

For equines, "Stallion Semen Immediate Use", the parameters are volume of gel-free semen, number of doses per collection, motile sperm per dose, and motility. Calculated, but not directly modifiable values, include volume gel-free semen and recommended volume of extender per dose.

For equines, "Stallion Semen Cooled and Shipped", the parameters include volume of gel-free semen, motile sperm per dose, motility, number of doses per collection, dilution ratio (extender to gel-free semen), motile sperm concentration per dose, volume of gel-free semen, and insemination dose volume. As above, when one of these values is modified, the rest of the parameters are automatically re-calculated and displayed.

After selection of the desired semen dose, the operator can request to have a semen evaluation or transported semen report printed by a computer or printer. Each report is customized based on the particular species selected.

Densimeter Control Serial Communications Routines

Communication between the densimeter and a personal computer or printer is provided via the RS232C serial communication port 6 on the front panel of the unit. The serial port is configured to transmit/receive at 1200 BAUD using the standard three wire configuration with the addition of clear to send, and data set ready connections. If the Densimeter is connected to a personal computer, the computer can assume complete operational control.

The densimeter computer services the communication port by means of a hardware interrupt. When a transmission is detected, the densimeter suspends its current operation and receives the transmission, which is then parsed to determine if one of the six commands listed below was received. Valid serial communication commands are:

ID: The identify command instructs the densimeter to transmit the unit serial number and a description of the currently selected animal and operation to the personal computer PC.

SND: The send command instructs the densimeter to receive a block of data from the PC and to store it into the specified memory location.

GET: The get date command instructs the densimeter to send a block of data from its internal memory to the PC.

PGM: The program command instructs the densimeter to receive a new calibration or protocol from the PC and to translate it into the system.

DEL: The delete command instructs the densimeter to delete the last program loaded.

EXE: The execute command instructs the densimeter computer to execute an internal subroutine residing at the location specified by the PC. Upon completion, the densimeter computer resumes execution of the main program from where it left off.

One of the important features of the densimeter of the present invention is the built in "expert system" which automatically optimizes the number of motile sperm cells, number of insemination doses per collection, recommended volume of extender, total insemination volume, dilution ratio, total sperm per dose, and motile sperm concentration based on the selected usage protocol. This capability is a substantial change from the original densimeter which required that the operator make these decisions.

The "expert system" bases it's recommendations on a set of internally programmed rules which are included with each semen processing protocol. All recommendations can be over-ridden by a knowledgeable operator if desired.

For STALLION SEMEN IMMEDIATE USE, the system initially recommends that the operator use 500 million motile sperm per dose. The volume of semen per dose is calculated using the equation in the previous text. The number of doses per collection is calculated based on the total volume of semen and the volume of semen per dose. The densimeter then recommends a volume of semen based on the following rules: a) minimum volume of extender will be 10 ml., and b) the volume of extender is automatically increased to maintain a 1:1 dilution ratio.

For STALLION SEMEN COOLED AND SHIPPED, the system initially recommends that the operator use 1 billion motile sperm per dose. As above, the volume of semen per dose and the number of doses per collection is calculated. The densimeter then dilutes the motile sperm concentration (number of motile sperm per milliliter of insemination dose) to 25 million sperm per millimeter. The dilution ratio of extender to semen is checked to insure that a minimum dilution ration of 3:1 is used. If the dilution is less than the recommended 3:1 ration, the densimeter increases the volume of extender (thereby reducing the motile sperm concentration) until the recommended dilution ratio is achieved. The expert system then calculates the volume of extender to add to the entire ejaculate prior to division into individual doses.

We claim:

1. In an instrument for measuring sperm concentration of a semen specimen and calculating dose value and having an optical assembly with a light source, a specimen holder and a photodetector, a computation means and a display, the improvement comprising in combination:

storage means for storing a concentration and calibration calculation equation in the form of a continuous multi-term polynomial obtained from a plurality of data points and directly relating measured sperm concentration and measured sperm transmittance value so that separate calibration of said light source is omitted;

said computation means including means for calculating sperm concentration of a semen specimen independently of the optical absorbance of the semen specimen using said stored concentration and calibration calculation equation and a semen specimen transmittance value;

said optical assembly including means for measuring transmission of said specimen holder while empty with said light source energized, TFS, sample transmission of said specimen holder with a semen specimen with said light source energized, TS, and dark cell output of said photodetector with said light source unenergized, TDC;

said computation means including means for calculating actual percent transmission of the semen specimen in said specimen holder as follows (TS−TDC)/(TFS−TDC) to provide a transmittance value for the semen specimen;

said means for measuring including means for making a plurality of said measurements and transmittance value calculations in sequence and calculating an average for said transmittance value.

2. An instrument as defined in claim 1 wherein said computation means includes means for calculating actual volume of semen to be used as a dose, D, as follows $$D = N/(CM),$$

where N is a total number of viable spermatozoa desired, C is calculated sperm concentration, and M is estimated percentage of sperm that are viable.

3. An instrument as defined in claim 2 wherein said light source includes a low power lens-end light emitting diode with a beam or narrow band red light and a dominant wave length of 660 nM and a collimating tube, and wherein said photodetector is an optically unfiltered silicon photodetector responsive to visible light in the red portion of the spectrum.

4. An instrument as defined in claim 1 including:

a set of data stored in said storage means, said data comprising recommended actions;

said computation means including means for selecting a recommended action following calculation of the sperm concentration of a semen specimen; and means for delivering the selected recommended action to said display.

5. A method of measuring sperm concentration of a semen specimen and calculating dose value for artificial insemination, including the steps of:

storing a concentration and calibration calculation equation in the form of a multi-term polynomial obtained from a plurality of data points and directly measured sperm concentration and measured sperm transmittance value whereby separate calibration of a light source is omitted;

measuring transmission of a specimen holder while empty with a light source energized to obtain a value TFS;

measuring transmission of the specimen holder with a semen specimen with the light source energized to obtain a value TS;

measuring dark cell output of the photodetector with the light source unenergized to obtain a value TDC;

calculating (TS−TDC)/(TFS−TDC) for the semen specimen providing a transmittance value for the semen specimen;

making a plurality of the measurements and calculation of transmittance value in sequence and calculating an average for the transmittance value; and calculating sperm concentration using the stored concentration and calibration calculation equation and the average transmittance value.

6. The method as defined in claim 5 including calculating actual volume of semen to be used as a dose, D, as follows:

$$D = N/(CM),$$

where N is total number of viable spermatozoa desired, C is calculated sperm concentration, and M is estimated percentage of sperm that are viable.

7. The method as defined in claim 5 including:

storing a set of data comprising recommended actions;

after calculating sperm concentration selecting a recommended action from the stored set of data; and displaying the recommended action for the operator.

8. An instrument having a storage means which contains data representing the concentration and calibration calculation equation of claim 5.

* * * * *